United States Patent [19]
Urie et al.

[11] Patent Number: 5,059,197
[45] Date of Patent: Oct. 22, 1991

[54] LESION LOCATION DEVICE

[76] Inventors: Robert G. Urie, 3 Orchard Grove, Flackwell Heath, Buckinghamshire, HP10 9PT; Ian O. Ellis, Yew Tree House, 2 Kenilworth Road, The Park, Nottingham, NG7 1DD, both of United Kingdom

[21] Appl. No.: 509,894

[22] Filed: Apr. 16, 1990

[30] Foreign Application Priority Data

Apr. 15, 1989 [GB] United Kingdom ............... 8908575

[51] Int. Cl.⁵ .............................................. A61B 17/34
[52] U.S. Cl. ................................... 606/116; 604/264; 604/164; 128/657; 128/658
[58] Field of Search ................... 128/653 R, 654, 657, 128/658, 722, 116; 604/158, 164, 264, 280–281; 606/116

[56] References Cited

U.S. PATENT DOCUMENTS

| | | | |
|---|---|---|---|
| 3,836,775 | 9/1974 | Gullekson | 250/312 |
| 4,582,061 | 4/1986 | Fry | 128/329 R |
| 4,616,656 | 10/1986 | Nicholson et al. | 128/653 R |
| 4,774,948 | 10/1988 | Markham | 128/329 R |
| 4,950,228 | 8/1990 | Knapp et al. | 604/281 |
| 4,958,642 | 9/1990 | Christian et al. | 128/657 |

FOREIGN PATENT DOCUMENTS 2180760 3/1986 United Kingdom .
8806864 9/1988 World Int. Prop. O. .

OTHER PUBLICATIONS

Judkins, "Selective Coronary Arteriography", Radiology, vol. 89, No. 5, pp. 815–824 (1967).
Kopans et al, "Spring Hookwire Breast Lesion Localizer", Radiology 1985; 157:53738.

*Primary Examiner*—Lee S. Cohen
*Assistant Examiner*—John D. Zele
*Attorney, Agent, or Firm*—Lorusso & Loud

[57] ABSTRACT

A lesion location device suitable for marking a lesion in breast tissue comprises a wire, of which the first portion which has been bent to form a second portion at an obtuse or acute angle to the first portion, a 180° bend and a third portion which extends adjacent the second portion and continues beyond the bend in a direction substantially opposed to that of the second portion. The bend is resiliently pivotable and forms a spring mechanism to prevent ingress of the wire once in position in the lesion. Two graduated cannulas are also provided, one with a pointed end and one with a blunt end, which are suitable for the wire to be passed into them.

10 Claims, 2 Drawing Sheets

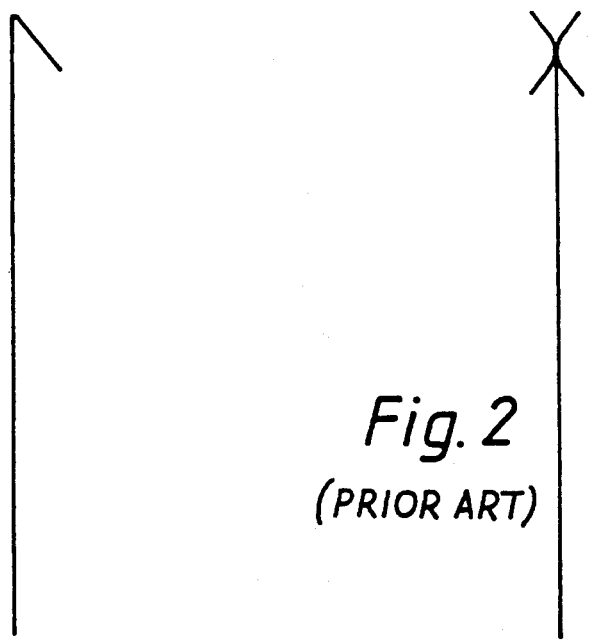
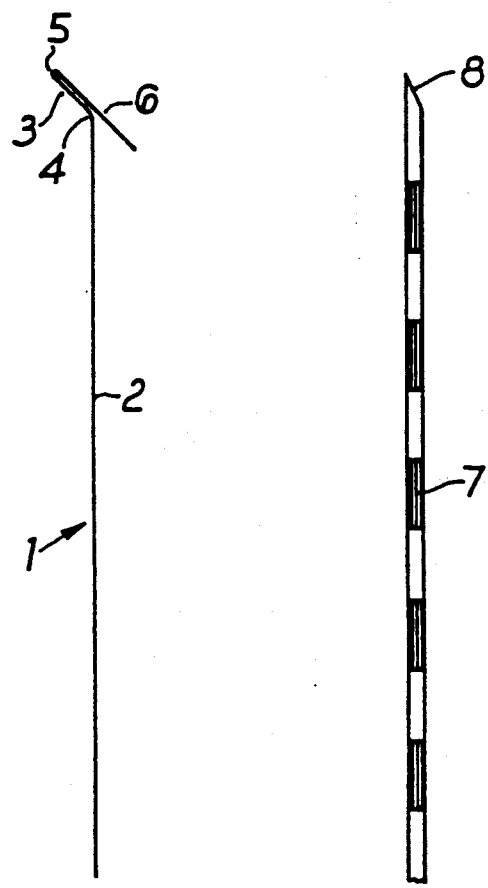
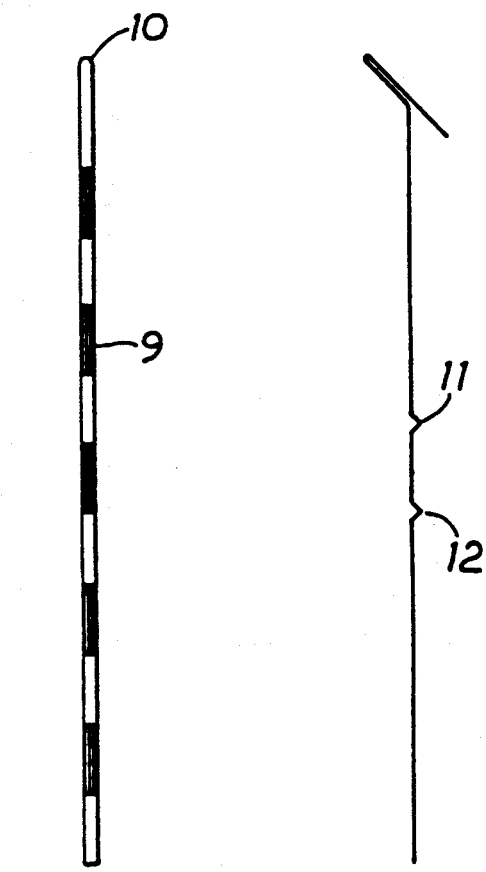
Fig. 1 (PRIOR ART)   Fig. 2 (PRIOR ART)   Fig. 3   Fig. 4   Fig. 5   Fig. 6

LESION LOCATION DEVICE

This invention relates to a lesion location device and more particularly to a barbed wire and cannulas suitable for marking a lesion in breast tissue.

When surgery is required to remove a lesion in tissue, it is necessary to mark the site in the tissue for the surgeon. The existing method consists of introducing a barbed wire into the site of the lesion and relying on the barb to ensure that the wire does not move in the tissue. There are two types of barb commonly in use. The first is merely an angled tip to the wire which is formed by bending the end of the wire so that it forms an acute angle of approximately 45° with the adjacent portion of the wire. The second consists of two curved pieces of wire which are joined at their respective mid-points to the end of a straight wire such that the ends of the curved pieces of wire form angles of approximately 45° and 135° with the longitudinal axis of the straight wire, the direction of curvature of the two pieces of wire being substantially opposed to each other. The first type of barb suffers from the problem of ingress and may therefore incorrectly indicate the site of the lesion. The second type of barb may be awkward to remove from the tissue sample marking subsequent pathological examination very difficult.

The invention seeks to provide a more effective device.

The invention provides a device suitable for marking a site in tissue comprising a barbed wire and a hollow cannula characterised in that the wire consists of an elongate first portion, a second portion which forms an angle with the first portion and which is resiliently pivotable about its point of junction with the first portion, and third portion which extends adjacent the second portion for at least part of the length of the second portion and then continues beyond the said point of junction in a direction substantially opposed to that of the second portion.

Advantageously, the first portion and the second portion are integrally formed with one another.

Desirably, the first portion, the second portion and the third portion are formed from a single piece of wire, a portion of the wire having been bent through an acute angle to form the second portion, a further portion then having been bent through approximately 180° at a point spaced from the said point of junction between the first portion and the second portion to form the third portion.

The angle between the first and second portions, measured when the device is in a relaxed configuration, may be 90°, acute or obtuse but is preferably obtuse.

Conveniently, the angle between the second portion and the first portion is between 150° and 120°, preferably 135° and the angle between the first portion and the part of the third portion which extends beyond the said point of junction is between 30° and 60°, preferably 45°. If the angle between the first and second portions is acute, then it is preferably 30°-60°, especially 45°.

Advantageously, the point of junction between the first portion and the second portion is sufficiently resiliently pivotable to allow the second portion to form an angle as close to 180° or 0° as possible with the first portion such that the wire may be placed inside a hollow cannula.

Desirably, the length of the second portion is 8 mm and the length of the third portion is 16 mm.

Preferably the hollow cannula is marked at intervals.

The invention will now be described in detail with reference to the accompanying drawings in which:

FIGS. 1 and 2 are respective side views of two barbed wires commonly used in the prior art and FIGS. 3 to 5 are respective side views of a barbed wire in accordance with the invention and two hollow cannulas used in connection with the barbed wire;

FIG. 6 is a side view of a further barbed wire in accordance with the invention;

EXAMPLE 1

Figure 7:
FIG. 7 is a representation of a side mammogram showing the wire of FIG. 3 marking the location of an impalpable lesion.

Referring to FIG. 3, the barbed wire 1 comprises a first portion 2 and a second portion 3 which is formed at an obtuse angle of approximately 135° to the first portion 2. The bend 4 between the first portion 2 and the second portion 3 is resiliently pivotable. At the end oof the second portion 3 remote from the bend 4 is a bend 5 of 180° from which extends a third portion 6. The third portion 6 extends parallel to the second portion 3 and continues beyond the bend 4 in a direction substantially opposed to the direction of extension of the second portion 3. The length of the second portion 3 is approximately 8 mm and the length of the third portion 6 is approximately 16 mm.

The barbed wire 1 is formed by appropriately bending a single piece of wire. It is typically 300 mm long and 36 gauge (0.193 mm diameter) size.

A hollow cannula 7, shown in FIG. 4, has a pointed end 8 and is typically an 18 gauge (1.24 mm) size, 90 mm long. Another cannula 9, shown in FIG. 5, has a blunt end 10 and is typically a 20 gauge (0.89 mm) size, 90 mm long. Both cannulas 7, 9 are marked at 1 cm intervals along their length.

The barbed wire 1 and cannulas 7 and 9 are made from BS 304 series (EN 58E) hypodermic needle grade stainless steel.

To mark the site of a lesion for surgery, the lesion is first identified with a stereotaxic device and the skin and needle tract anaesthetised. A small (1-2 mm) incision is then made in the skin at the entry point and the cannula 7 is inserted with a trocar (not shown). The trocar, a solid rod with an angled end to match the angle of the pointed end 8 of the cannula 7, fills the cannula to ease insertion, preventing the entry of any tissue in the the cannula during insertion. When the cannula is in position, the trocar is removed and the barbed wire 1 is inserted into the cannula up to the point of the cannula. In order to insert the barbed wire into the cannula, the second portion 3 is rotated at the bend 4 such that the second portion 3 and the third portion 6 extend in a direction as close to parallel with that of the first portion 2 as possible. The depth of the wire 1 is noted using the graduations of the cannula 7 and the cannula is then removed whilst holding the wire in place. Once the correct position of the wire 8 has been confirmed, it is fixed in position by coiling and taping to the skin, taking care not to bend the wire. The third portion 6 of the wire 1 holds the wire in position within the lesion against a pull and the bend 4 provides a spring mechanism which holds the wire in position against a push thus deterring ingress.

During surgery, the blunt cannula 9 is tracked down the wire 1 until the blunt end of the cannula rests against the second and third portions, 3, 6 and resistance is felt. The depth below the skin can be gauged by the graduations on the cannula 9. The wire is then clamped to the cannula. The end of the cannula 9 is palpable to the surgeon to aid the decision as to the best surgical approach.

The 180° bend 5 in the wire 8 may be achieved by a single bend of 180° or alternatively it may be formed by two 90° bends close to each other. The 180° bend 5 may be omitted completely and a third portion may be fused onto the second portion 3, but this adds to the manufacturing costs.

Instead of using a relatively large needle 7 the centre of which must be blocked with the trocar during entry to prevent "apple-coring", a smaller needle can be used, for example 21 gauge (0.810 mm) or 20 gauge (0.890 mm) with the blocking effect being achieved by the tip 5 of the barbed wire. The wire and needle are thus introduced simultaneously in a "free-hand" fashion, without the necessity for a sterotaxic apparatus, whilst the radiologist used ultrasound to guide the needle to the correct location.

EXAMPLE 2

Referring to FIG. 6, the barbed wire shown is substantially the same as that of FIG. 3 but includes two kinks 11, 12 approximately half way along the first portion of the wire and spaced from one another by about 1 cm. The kink 11 furthest from the barb can be used to indicate when the blunt cannula 9 has reached the obtuse angle bend 4 of the barb. The other kink 12 indicates when the tip 5 of the wire has reached the point of the needle.

The wires of the invention are particularly suitable for use in marking lesions such as tumours in living breast tissue but in principle may be used in other living tissue or in substances in vitro. Any radio-opaque, non-toxic (when used in vivo) material of sufficient flexibility and strength may be used.

EXAMPLE 3

Figure 9:
FIG. 9 is a side view of a further device of the invention.
Figure 8:
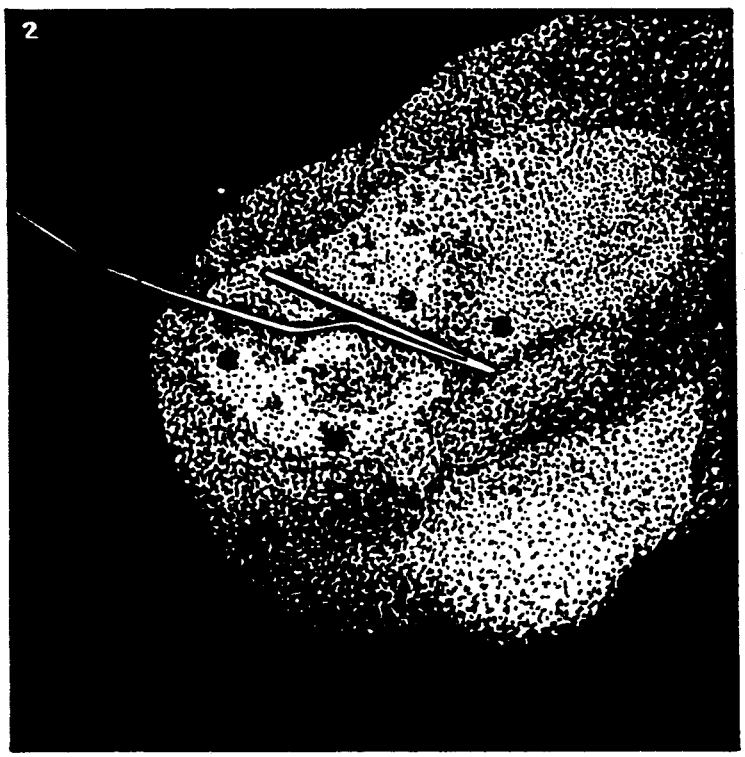
FIG. 8 is a representation of a radiograph of the resected specimen from the same patient as FIG. 7, demonstrating accurate surgical resection of the lesion.

Referring to FIG. 9, a further wire in accordance with the invention is the same as the wire of FIG. 3 but the angle between the said first and second portions is acute, namely substantially 45°.

We claim:

1. A device suitable for marking a site in tissue comprising a barbed wire wherein the wire consists of an elongate first portion, a second portion which forms an angle with the first portion and which is resiliently pivotable about its point of junction with the first portion, and a third portion which extends adjacent the second portion for at least part of the length of the second portion and then continues beyond the said point of junction in a direction substantially opposed to that of the second portion.

2. A device according to claim 1 wherein the first portion and the second portion are integrally formed with one another.

3. A device according to claim 1 wherein the angle between the first and second portions is obtuse.

4. A device according to claim 3 wherein the first portion, the second portion and the third portion are formed from a single piece of wire, a portion of the wire having been bent through an acute angle to form the second portion, a further portion then having been bent through approximately 180° at a point spaced from the said point of junction between the first portion and the second portion to form the third portion.

5. A device according to claim 3 wherein the angle between the second portion and the first portion is between 150° and 120° and the angle between the first portion and the part of the third portion which extends beyond the said point of junction is between 30° and 60°.

6. A device according to claim 5 wherein the angle between the second portion and the first portion is substantially 135° and the angle between the first portion and the part of the third portion which extends beyond the said point of junction is substantially 45°.

7. A device according to claim 1 wherein the angle between the first and second portions is acute.

8. A device according to claim 1 wherein the point of junction between the first portion and the second portion is sufficiently resiliently pivotable to allow the second portion to form an angle as close to 180° or 0° as possible with the first portion such that the wire may be placed inside a hollow cannula.

9. A device according to claim 1 wherein the length of the second portion is substantially 8 mm.

10. A kit comprising a device according to claim 1 and a hollow cannula marked at intervals.

* * * * *